United States Patent
Perret et al.

(10) Patent No.: US 9,212,998 B2
(45) Date of Patent: Dec. 15, 2015

(54) METHOD AND DEVICE FOR THE SPECTRAL ANALYSIS OF A METAL COATING LAYER DEPOSITED ON THE SURFACE OF A STEEL STRIP

(75) Inventors: Jean Perret, Montbrison (FR); Marc Michaut, L'Horme (FR); Laurent Cloutot, Killwangen (CH)

(73) Assignee: Primetals Technologies SAS France, Saint-Chamond (FR)

( * ) Notice: Subject to any disclaimer, the term of this patent is extended or adjusted under 35 U.S.C. 154(b) by 820 days.

(21) Appl. No.: 13/319,224

(22) PCT Filed: May 28, 2009

(86) PCT No.: PCT/EP2009/056564
§ 371 (c)(1),
(2), (4) Date: Dec. 9, 2011

(87) PCT Pub. No.: WO2010/127713
PCT Pub. Date: Nov. 11, 2010

(65) Prior Publication Data
US 2012/0076922 A1    Mar. 29, 2012

(30) Foreign Application Priority Data

May 7, 2009  (EP) .................................. 09290338

(51) Int. Cl.
*G01N 21/71* (2006.01)
*B23K 26/00* (2014.01)
(Continued)

(52) U.S. Cl.
CPC ............ *G01N 21/718* (2013.01); *B23K 26/009* (2013.01); *B23K 26/032* (2013.01);
(Continued)

(58) Field of Classification Search
CPC .. B23K 26/0846; B23K 26/40; B23K 26/032; B23K 26/0661; B23K 26/009; G01N 21/8914; G01N 21/718; C23C 2/003; B60P 1/52
See application file for complete search history.

(56) References Cited

U.S. PATENT DOCUMENTS

| 1,240,212 | A | | 9/1917 | Horvath |
| 3,762,822 | A | * | 10/1973 | Harvey et al. .................. 356/429 |

(Continued)

FOREIGN PATENT DOCUMENTS

| DE | 4138157 A1 | 5/1993 |
| DE | 10361727 B3 | 7/2005 |

(Continued)

OTHER PUBLICATIONS

New approach to online monitoring of the Al depth profile of the hot-dip galvanised sheet steel using LIBS, Herbert Balzer . Manuela Hoehne, Reinhard Noll. Volker Sturm, Anal Bioanal Chem (2006) 385: 225-233, 2006.*

(Continued)

*Primary Examiner* — David Turocy
*Assistant Examiner* — Mohammad Mayy
(74) *Attorney, Agent, or Firm* — Laurence Greenberg; Werner Stemer; Ralph Locher (57) ABSTRACT

In a method for the spectral analysis of a metal coating layer deposited on the surface of a steel strip, the strip is moved along an arc of the outer surface of a rotating roller with a cylindrical wall guiding the strip by contact. An ablation laser beam is guided into an internal cavity of the cylindrical wall to be placed in optical incidence under a normal axis on the outer surface of the roller on a targeted contact point of the strip and the roller. The beam passes through the wall via a wall opening, which is transparent to the beam. A plasma spectral emission distribution from the laser ablation to the contact point is collected by optical feedback in the direction of the normal axis on the outer surface of the roller and through the opening in order to be guided towards a spectral measurement unit. The normal axis on the outer surface for the optical incidence and feedback is placed in synchronous rotation with the roller.

11 Claims, 4 Drawing Sheets

(51) Int. Cl.
  *B23K 26/03* (2006.01)
  *B23K 26/06* (2014.01)
  *B23K 26/08* (2014.01)
  *B23K 26/40* (2014.01)
  *C23C 2/00* (2006.01)
  *G01N 21/89* (2006.01)

(52) U.S. Cl.
  CPC ......... *B23K26/0661* (2013.01); *B23K 26/0846* (2013.01); *B23K 26/40* (2013.01); *C23C 2/003* (2013.01); *G01N 21/8914* (2013.01)

(56) References Cited

U.S. PATENT DOCUMENTS

| | | | |
|---|---|---|---|
| 5,798,832 | A | 8/1998 | Hnilica et al. |
| 7,164,955 | B2 | 1/2007 | Moreas et al. |
| 2003/0016353 | A1 | 1/2003 | Detalle et al. |
| 2005/0012244 | A1 | 1/2005 | Jones |
| 2007/0240325 | A1* | 10/2007 | Pelsue et al. .................... 33/707 |
| 2007/0296966 | A1 | 12/2007 | Benicewicz et al. |

FOREIGN PATENT DOCUMENTS

| | | |
|---|---|---|
| JP | 2003121363 A | 4/2003 |
| JP | 2006317379 A | 11/2006 |
| KR | 2007167785 A | 6/2006 |
| WO | 0008446 A1 | 2/2000 |
| WO | 02101366 A1 | 12/2002 |

OTHER PUBLICATIONS

Laser Induced Breakdown Spectroscopy for Elemental Process Monitoring of Slurry Streams, J. D. Winefordner, Florida Institute of Phosphate Research, 2000.*
Online coating thickness measurement and depth profiling of zinc coated sheet steel by laser-induced breakdown spectroscopy, H. Balzer, M. Hoehne, V. Sturm, R. Noll, Spectrochimica Acta Part B 60 (2005) 1172-1178, 2005.*
DE 4138157 A1, machine translated.*
Giorgi et al., "Modelling of the galvanizing reactions" La Revue de Metallurgie-CT, Oct. 2004—English abstract on p. 840.
Orzi et al., "Identification and Measurement of Dirt Composition of Manufactured Steel Plates Using Laser-Induced Breakdown Spectroscopy", Applied Spectroscopy, vol. 58, No. 12, 2004, XP002560629.
Balzer et al., "Online coating thickness measurement and depth profiling of zinc coated sheet steel by laser-induced breakdown spectroscopy", Spectrochimica, Act A, Part B, vol. 60, 2005, pp. 1172-1178, XP002560625.
Balzer et a.l, "New approach to online monitoring of the Al depth profile of the hot-dip galvanised sheet steel using LIBS", Anal Bioanal Chem, 2006, pp. 225-233.

* cited by examiner

METHOD AND DEVICE FOR THE SPECTRAL ANALYSIS OF A METAL COATING LAYER DEPOSITED ON THE SURFACE OF A STEEL STRIP

BACKGROUND OF THE INVENTION

Field of the Invention:

The present invention relates to a method and a device for the spectral analysis of a metal coating layer deposited on the surface of a steel strip.

The invention relates in particular to the quality control of a metal coating deposited by dipping a continuously moving metal strip, for example a zinc-alloy coating having undergone an alloying process.

Hot dip galvanizing of continuously moving rolled steel strips is a well-known technique. It essentially comprises two variants: one where the strip leaving the galvanizing furnace descends obliquely into a bath of molten zinc and is diverted vertically upwards by a roll immersed in said molten zinc. The other variant involves diverting the moving steel strip vertically upwards as it leaves the furnace, before passing it through a vertical channel containing molten zinc sustained magnetically.

The formation kinetics of this deposition would be known to a person skilled in the art and has been disclosed on numerous occasions, including in "Modeling of galvanizing reactions" by Giorgi et al. in "La Revue de Métallurgie CIT" in October 2004. This documentation establishes that contact between the molten coating mixture and the strip causes dissolution of the iron from the steel strip that, firstly, participates in the formation, on the surface of the strip, of a compound layer of approximately 0.1μ of the compound $Fe_2Al_5Zn_x$ and, secondly, spreads to the bath of molten mixture until the $Fe_2Al_5Zn_x$ layer has formed continuously. The $Fe_2Al_5Zn_x$ layer serves to support the protective zinc layer while the dissolved iron contributes to the formation of precipitates comprising Fe, Al and Zn, known as "dross", in the molten mixture.

The coating of steel strips with a zinc-based metal alloy has numerous applications, for example in car bodywork, domestic appliances and construction. Several coatings stand out on account of their composition and possible treatment once applied to the strip.

One such coating undergoes an "alloying" process by reheating, which uses diffusion to form an alloy between the iron in the steel and the zinc in the coating. This type of coating is generally referred to by the abbreviation "GA" or the term "galvanneal". GA galvanizing provides good protection of the steel against corrosion and certain specific qualities, such as the porosity and surface texture thereof, making it moreover particularly suitable for paint, of which it increases the adherence, and facilitating resistance welding of the coated strips. For these reasons, it is primarily used in the automotive industry.

The iron/zinc alloy of a GA coating may be provided in the form of several phases having different crystallographic meshes and compositions. In order to ensure that the coating provides optimum characteristics for deep drawing and painting, studies have shown that the iron content in the surface of the coating must be low without reaching zero. Numerous parameters are liable to affect the microstructure of the galvanneal layer—the chemical composition of the strip and the chemical composition of the coating bath, the surface roughness of the strip, the temperature of the coating bath and, above all, the temperature in the alloying furnace and the speed of movement of the strip.

Studies have been carried out to define means for tracking the development of zinc, iron and aluminum content through the thickness of the galvanneal deposits in order to better understand the influence of each parameter and to monitor the quality of the coated strips. Several methods for determining the concentration profile of elements of alloys on samples of coated strips have been proposed, including "Glow discharge optical emission spectroscopy GD-OES" and "Laser-induced breakdown spectroscopy LIBS" spectroscopic measurement.

Document WO 00/08446 discloses the basis for such an analysis method using laser ablation (LIBS) and document US 2003/0016353 provides a number of improvements intended to increase the accuracy of measurements.

Nonetheless, the analysis methods described are very difficult to implement for use in real time on a galvanizing line where the strip is moving at speeds of up to more than 3 meters per second.

Indeed, in a known manner, the LIBS method uses the interaction between laser and matter to heat a target to be analyzed to a very high temperature and to generate spectral lines characteristic of the material heated at the target point of the strip. A pulsed laser is therefore fired at the target for a very short time, around 10 nanoseconds, at a power of several tens of millijoules aimed at a very weak surface. A microplasma is created that emits a continuum of radiations and, after a few microseconds, the first spectral lines appear, said lines being characteristic of the material of which the target, and therefore the strip coating, is made. A spectrometer is used to perform a spectral analysis of the light emitted during a measurement period during the microseconds following the laser shot, when the background noise of the continuum is sufficiently reduced.

During a single microsecond's delay between the laser firing and the spectrometer measurement, and for a movement of around 3 meters per second, the strip and therefore the target and the plasma are moved 3 millimeters. To take a measurement on a moving target, a person skilled in the art would create a positional offset between the firing axis of the laser and the optical axis of the measurement device, which is very difficult to achieve with sufficient precision, especially as the speed of movement of the strip during galvanizing can vary significantly as a function of the thickness of said strip, the heating capacity of the galvanizing furnace, the thickness of the coating in question, and the performance of the devices for drying the liquid coating.

Furthermore, intrinsic vibrations or deformations in the strip or the trajectory of movement thereof make said measurement very inaccurate, given that a local targeting precision of a few microns is required. An article entitled "New approach to online monitoring of the Al depth profile of the hot dip galvanized sheet steel using LIBS", H. Balzer et al., published on Mar. 29, 2006, Springer Verlag 2006, discloses for this purpose a sample system using complex vibration offsetting. This article mentions that this system is designed for low strip movement speeds (less than 1 m/s) while the speeds required in an industrial context may be around 3 to 4 m/s. Such a system would therefore be unable to offset the resulting vibrations.

BRIEF SUMMARY OF THE INVENTION

An object of the present invention is to enable a spectral analysis measurement of a metal coating layer deposited on the surface of a steel strip, said measurement being appropriate in consideration of the fact that said strip is moving. It should be noted that the strip may be of different sizes or different movement speeds, potentially above 1 m/s.

Using a method for the spectral analysis of a metal coating layer deposited on the surface of a steel strip, the invention is characterized by the following steps:

- said strip is moved along an outer-surface arc of a rotating roll having a cylindrical wall guiding the strip by contact,
- a "laser ablation" beam is delivered via an internal cavity to the cylindrical wall such that it is optically incident, along an axis normal to the outer surface of the roll, on a target contact point of the strip and the roll, said beam passing through the wall via a wall opening, which is transparent to the beam;
- a spectral plasma emission distribution from the laser ablation of the contact point is collected by optical feedback along the axis normal to the outer surface of the roll and through the opening in order to be delivered to a spectral measurement unit,
- the axis normal to the outer surface used for optical incidence and feedback is moved in rotation synchronous to the roller.

The roll may advantageously be a drive roll or bearing roll of any type, such as a strip drive roll or a guide roll driven by the strip. A key aspect is that the measurement method according to the invention ensures that the strip is and remains in contact on the arc portion (for example at 90°) so that the target point of the laser is exactly at the intersection of the outer surface of the roll and of the strip coating. Thus, any risk of taking a measurement outside of the desired range is eliminated, because all vibrations of the moving strip are completely attenuated. The roll exerts a natural tension facilitating a perfect flattening of the strip against the outer surface of said roll. Related tensioning systems between the roll and the strip can in any case be incorporated for this purpose.

This method may be implemented using a simple device having multiple alternative embodiments, which in particular facilitate installation thereof on the rolls in a steel-strip processing line.

In particular, such a device for implementing the method according to the invention, as adapted for the spectral analysis of a metal coating layer deposited on the surface of a steel strip, may be characterized by:

- a "laser ablation" beam emitter and a spectral plasma emission receiver,
- a first optical route arranged at the output of the emitter, designed to guide the laser ablation beam through the roll cavity and having an optical guiding means to ensure the incidence of said beam on the target contact point,
- a second optical route arranged at the input of the receiver and designed to collect the spectral plasma emission distribution through said optical guiding means,
- at least the optical guiding means is rotatable by a mechanical coupling synchronous to the rotation of the roll.

In order to ensure a given incidence of the laser and optical feedback of the plasma distribution at the target point, the optical guiding means may include a dichroic mirror inclined at 45° to the normal axis and the axis of rotation of the roll. This mirror enables the incident beam and the optical feedback beam to be directed along the normal axis, and it allows a single optical path to be used on the normal axis. The dichroic mirror is therefore at least arranged on the normal axis.

Advantageously, the first optical route may include a light guide, such as an optical fiber or an air guide that make it possible to improve distribution, i.e. to deliver the incident light or to guide the light emitted by the plasma to the target point directly or via the dichroic mirror respectively by reflection and/or by transmission. An alternative embodiment of the device provided with a dichroic mirror can also be realized by replacing it with at least one total reflection mirror.

Similarly, the second optical route may include a light guide, such as an optical fiber or an air guide in order to deliver the plasma distribution beam to the receiver.

Instead of a dichroic mirror placed inside the cavity of the roll (on the normal axis), the first and second optical routes may comprise at least one optical fiber having a 90° elbow as an optical guiding means thereby delimiting a fiber zone alongside the axis of rotation of the roll and a fiber zone alongside the axis normal to the target contact point.

The arrangement of a dichroic mirror is however noticeably outside the cavity of the roll, such as to separate the two beams leaving the emitter and entering the receiver if they are served by a single fiber (or a bundle of several fibers) on the same side of the roll.

As a function of the multiple configuration requirements sought, the device according to the invention may be adapted flexibly. Indeed, the invention provides for the placement of at least the emitter and/or the receiver outside the internal cavity of the roll. Moreover, this makes it possible to easily install a LIBS instrument without major complex work in the cavity of the roll. In this case, optical joints (collimators, lenses, etc.) or mechanical joints (rotary joints) are required to ensure an energy link between these elements and/or an optical link depending on whether or not the LIBS (emitter and/or receiver) is turning with the roll.

Indeed, the emitter and/or receiver may be coupled in synchronous rotation with the optical guiding means, particularly if it is placed inside the cavity of the roll, in which case it is also coupled to an electrical link to the rotary joint, ideally for a power supply, a command signal and/or a control signal thereof.

The opening on a part known as the roll shell includes a porthole made of material that is optically transparent or permeable to the laser ablation beam and to the spectral plasma emissions induced by the ablation. This ensures that the face of the strip and the coating thereof in contact with the surface of the roll is not marked when it passes over the firing window made in the shell of the roll, the latter containing said porthole the external surface of which is carefully connected to the edges of the window-shaped opening.

Several different uses of the device implementing the method according to the invention are possible, in particular for a chemical analysis measurement of the coating surface of a steel strip moving on a roll following a galvanizing process.

In this regard, it is possible to obtain a very accurate measurement repeated almost continuously (on account of the high frequency of the laser pulses), said measurement being possible because even if the target is turning in contact with the roll, the target point remains the same in relation to the roll since it is moving on the contact arc (defined in relation to a fixed reference point on the ground, for example an angle of 90° over the 360° of the roll). Experience has in particular demonstrated that the following series of process steps is particularly suited to such a use of the device:

- temporally successive ablation laser beams fired to different depths of the strip at the same contact point of the moving strip with the roll in rotation, said point being the firing target,
- chemical analysis measurements related to each of the lasers fired at said target point.

at least one of the ablation lasers is fired to a depth:
a) of between 0 and 3 micrometers of the outer surface of the coating of the strip, ideally between 1 and 2 micrometers,
b) of around 40-60% of the depth of the coating,
c) of around 90-95% of the depth of the coating.

Evidently, these parameters may be adapted depending on the size and characteristics of the strip and the coating thereof. In particular, as the measurement enables precise spectral analysis, the method according to the invention may independently determine whether, as a function of the presence or absence of a targeted element of the coating, another laser should be fired to a greater or lesser depth to rectify this.

Use of the device for implementing the method according to the invention is also proposed to control the parameters determining the settings of an installation implementing the galvanizing method and determining the settings of an alloying furnace downstream of the galvanizing installation. Indeed, as the chemical analysis of the coating is very reliable, it can also be used to indicate any divergence of said coating obtained from a desired coating, adapting the settings of the coating installations to minimize such divergences.

The use of the device for implementing the method according to the invention therefore also provides a means for monitoring real-time operational data of the galvanizing process in relation to reference data. Indeed, as the analysis measurement is carried out on the moving strip without the need to slow it down or to stop it, a real-time adjustment loop is advantageously possible.

Finally, the device for implementing the method according to the invention may consequently be used to establish high-performance control scenarios as a function of parameters selected to ensure the operating data obtained falls within reference data tolerance levels. The method according to the invention is therefore made increasingly independent to provide coatings having characteristics that require specific tolerances.

In particular, the use of the device to control a hot-dip galvanizing installation for continuously moving steel strip is therefore characterized by the use of measurements, taken at several depths, of the concentrations of certain alloy elements in the coating, such as iron, aluminum and zinc, the measurements being taken on the moving strip by a laser-ablation spectrometry analysis device. For this purpose, the data captured by the analysis device is used by the PLC system of the galvanizing installation to control the heating power of the alloying furnace as a function, in particular, of the speed of movement of the strip.

Furthermore, the data captured by the analysis device is sent to a process optimization system along with other data recorded or measured, such as size, chemical composition, surface roughness of the strip, chemical composition and temperature of the coating bath, power of the alloying furnace and strip movement speed.

This process optimization system is able to assess the relevance of the operating data on the process in relation to a predetermined, stable, optimum operating range of the installation. This operating range may be, for example, the envelope of strip movement speeds possible as a function of all of the other parameters. This optimization system can therefore also offer potential process performance improvement scenarios within said stable, optimum operating range. These scenarios are based on adaptive control strategies, which may be the same type as the ones used in the PLC system of the installation.

BRIEF DESCRIPTION OF THE SEVERAL VIEWS OF THE DRAWING

Examples of the invention in these different categories are provided using the figures described:

FIG. 2 Diagram of variations in zinc, iron and aluminum concentrations in a GA coating, FIG. 3A Chemical analysis device according to a first embodiment of the invention, FIG. 3B Chemical analysis device according to a second embodiment of the invention, FIG. 4 Chemical analysis device according to a third embodiment of the invention, FIG. 5 Chemical analysis device according to a fourth embodiment of the invention, FIG. 6 Chemical analysis device according to a fifth embodiment of the invention, FIG. 7 Chemical analysis device according to a sixth embodiment of the invention.

DESCRIPTION OF THE INVENTION

Figure 1:
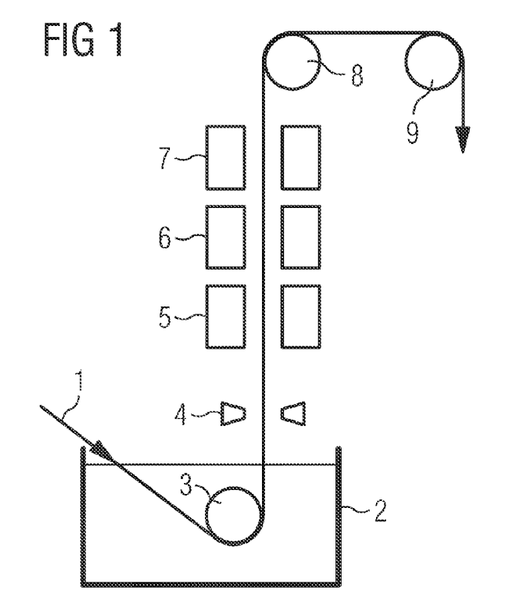
FIG. 1 General diagram of hot-dip galvanizing of a moving steel strip.

FIG. 1 is a general diagram of hot-dip galvanizing of a moving steel strip (1): the strip (1) coming from a galvanizing furnace is immersed in a liquid coating bath (2) and is diverted vertically by a roll (3) immersed in the bath. The strip then passes sequentially before a drying device for the liquid film (4), into an induction-heating device (5), into a device (6) for maintaining alloying temperature and into a cooling device (7) where the coating film solidifies. The strip is then partially coiled around a first deflector roll (8) then a second roll (9) before continuation of transformation operations and re-coiling on galvanized coils.

Figure 2:
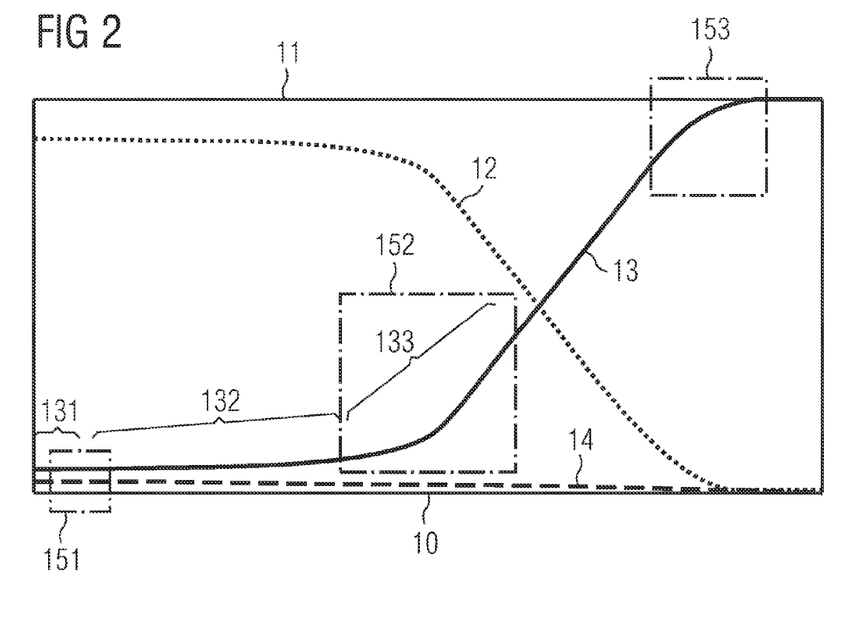

FIG. 2 is a sample diagram of variations in zinc, iron and aluminum concentrations in a GA coating: the x-axis (10) represents a depth variation in the coating, the surface of said coating being at the intersection with the y-axis (11), which represents the variations in concentration of the different elements zinc, iron and aluminum: the curve (12) represents the variation in zinc content, the curve (13) the variation in iron content and the curve (14) the variation in aluminum content. A first interval (131) showing limited depth variations in the curve (13) corresponds to a first iron/zinc alloying phase, known as type ζ, a second interval (132) showing moderate depth variations corresponds to a second phase, known as type δ, and a third interval (133) corresponds to a third phase, known as type Γ. In relation to each of these phases, a first framework zone (151) of the diagram therefore corresponds to a preferential zone for a first laser-ablation firing, and similarly second and third framework zones (152, 153) correspond to preferential zones for firings subsequent to the first firing.

Using this diagram, it is possible to define the reference parameters to implement the method according to the invention or to use a related device.

Figure 3A:
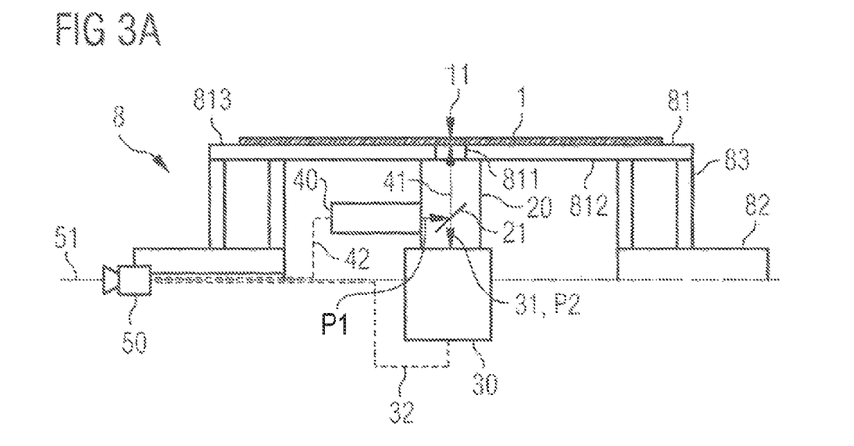

FIG. 3A shows a chemical analysis device according to a first embodiment of the invention, enabling the implementation of the aforementioned method and suitable for the spectral analysis of a metal coating layer deposited on the surface of a steel strip (1), in that:

said strip is moved along an outer-surface arc (813) of a roll (8) rotating about an axis (51) and having a cylindrical wall guiding the strip by contact, a "laser ablation" beam is delivered via an internal cavity to the cylindrical wall such that it is optically incident, along an axis (41) normal to the outer surface of the roll, on a target contact point (11) of the strip and the roll, said beam passing through the wall via a wall opening (811), which is transparent to the beam, a spectral plasma emission distribution from the laser ablation of the contact point is collected by optical feedback along the axis (41) normal to the outer surface of the roll and through the opening in order to be delivered to a spectral measurement unit, the axis normal to the outer surface used for optical incidence and feedback is moved in rotation synchronous to the roller.

The device shown for this purpose therefore comprises:
a "laser ablation" beam emitter (40) and a spectral plasma emission receiver (30),
a first optical route (P1) arranged at the output of the emitter, designed to guide the laser ablation beam through the roll cavity and having an optical guiding means (20) to ensure the ablation laser causes said beam to hit the target contact point (11),
a second optical route (P2) arranged at the input of the receiver and designed to collect the spectral plasma emission distribution through said optical guiding means (20),
at least the optical guiding means (20) is rotatable by a mechanical coupling synchronous to the rotation of the roll (8, 81, 82, 83) to the surface (813) of the shell (81, 812, 813) from which the strip is moving.

The strip (1) is therefore partially coiled on to an arc of the roll (8) comprising the shell (81) thereof, two rotation (support) shafts (82) at each extremity thereof coupled to joint flanges (83). A window is opened in the shell to form the opening (811). An optical device acting as guiding means (20) adjoining a first optical route (P1) in the form of an air guide is arranged perpendicular to an inner surface (812) of the shell (81) and aims the laser beam fired from the emitter (40) at the surface of the strip (1) in contact with an outer surface (813) of the shell (81) through the window (811). This optical device comprises a dichroic mirror (21) that aims the laser beam fired by the emitter (40) at the target point (11) and permits the feedback, via the second optical route (P2) in the form of an air guide, of a light beam emitted by the plasma towards the spectronomy device, i.e. the receiver (30). The optical device also includes focusing lenses and the members required to attach the ablation and analysis device (not shown). The emitter (40) and the receiver (30) are respectively linked by cables (42, 32) coupling them to a rotary joint (50) itself connected to a fixed cable outside the roll that supplies the devices (40, 30) with the power they require to work, as well as distributing the signals controlling their activity (command, settings, control, alarms, etc.).

Accordingly, this device includes the optical guiding means (20) as a simple dichroic mirror inclined at 45° from the normal axis (41) and the axis of rotation (51) of the roll.

The first and second optical routes therefore comprise a light guide in the form of a simple air guide included in the guiding means (20).

The opening (811) includes a porthole made of material that is optically transparent to the laser ablation beam and to the spectral plasma emissions.

It should be noted that, in this embodiment, the emitter and the receiver are both arranged in the cavity inside the roll and rigidly attached to the roll to ensure a synchronous rotation of the normal axis (41).

However, it is only required that at least the emitter and/or receiver be coupled in synchronous rotation with the optical guiding means, particularly if it is placed inside the cavity of the roll, in which case it is also coupled to an electrical link (42, 32) having a rotary joint (50), ideally for power supply, a command and/or control signal, etc.

Figure 3B:
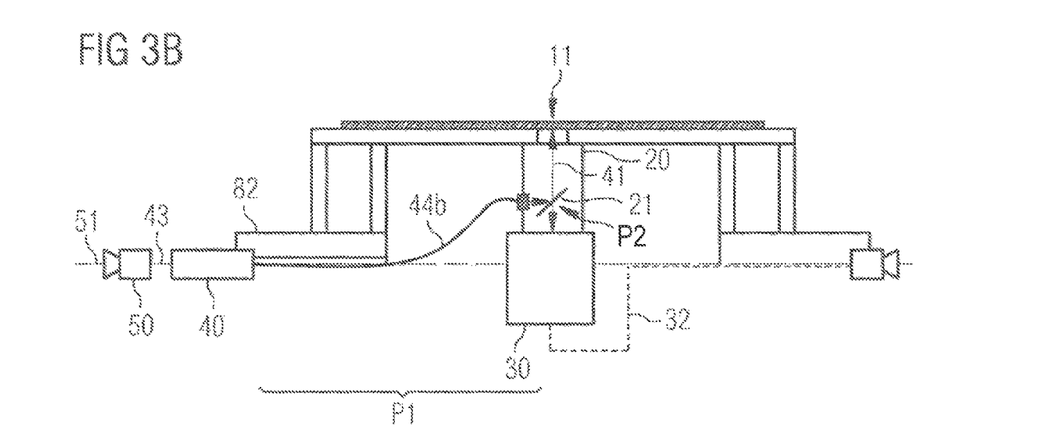

This latter alternative to FIG. 3A is shown in FIG. 3B, where the receiver (30) is placed in the cavity as in FIG. 3A, while the emitter (40) is placed outside the cavity, for example at one of the extremities of the roll. The emitter (40) can then be coupled mechanically to the axis of rotation (51) of the roll and consequently moves in synchronous rotation with the roll. In this case, the first optical route (P1) comprises a light guide that may take the form of an optical fiber (44b) coupled to the guiding means (20) or of an air guide (not shown) if the dichroic mirror (21) in the guiding means (20) is alternatively placed on the axis of rotation (51) thereby enabling the incident beam fired by the emitter (40) to be intercepted and diverted to the target point (11). This chemical analysis device according to a second embodiment of the invention therefore also provides in this case for the emitter and the receiver to be in synchronous rotation with the roll and the normal axis (41).

Finally, again as an alternative to FIG. 3A and similarly to the arrangement of the emitter according to FIG. 3B, the emitter and the receiver (40, 30) may both be arranged outside the cavity of the roll. The emitter and the receiver at the extremities may therefore be constrained to rotate synchronously with the roll shaft (or not, depending on the optic and the mechanical setup selected for the extremities).

Figure 4:
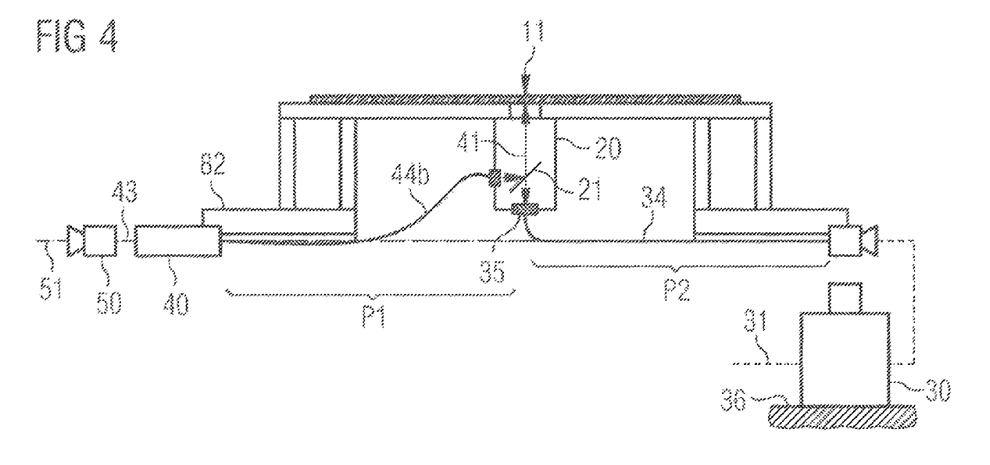

A similar arrangement is shown by a device according to a third embodiment shown in FIG. 4. The emitter and the receiver are respectively coupled via respectively the first and second optical routes (P1, P2) comprising an optical fiber (44b, 34) to the guiding means (20) ensuring the incidence and feedback of the light beams from an output of the optical fiber (44b) for incidence or towards an input of the optical fiber (34) for the feedback. Only the emitter (40) is in synchronous rotation with the roll and the normal axis (41) as in FIG. 3B. The receiver (30) is arranged non-rotatingly outside the cavity and the optical input thereof receiving the second optical route (P2) (having the optical fiber 34) providing on demand a rotary coupling coupled to the extremity of the optical fiber.

Figure 5:
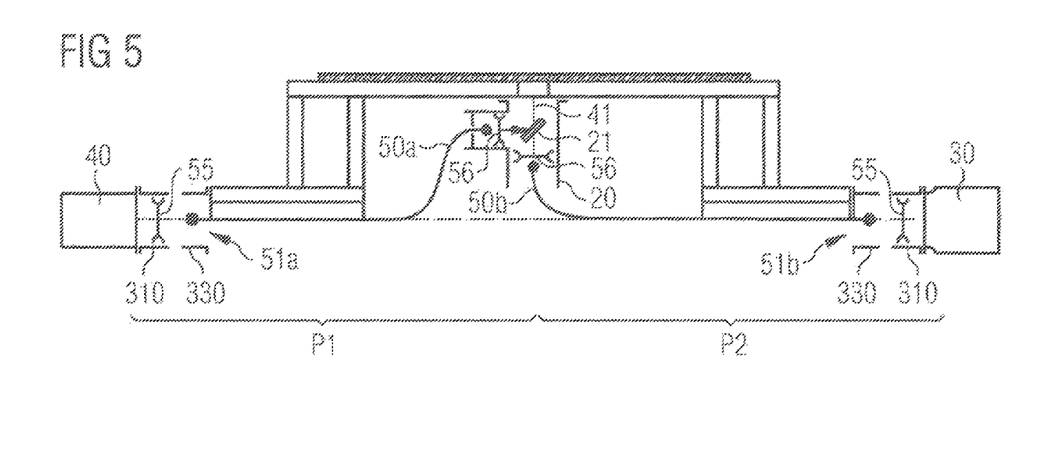

FIG. 5 shows a fourth embodiment of the device based partially on FIG. 4, in that the first and second optical routes (P1, P2) comprise respectively an optical fiber (50a, 50b) leading to a guiding means (20) provided with a dichroic mirror (21) and coupling optics (56) of the fibers and that is placed opposite the shell opening facing the target point. Unlike FIG. 4, the optical fibers (50a, 50b) defining the optical routes (P1, P2) are constrained to rotate synchronously with the roll and the input and output thereof to the extremities of the roll shaft. They are for example arranged in one of two apertures (51a, 51b) holding the fiber on the axis of rotation of the roll, the aperture receiving or emitting a light beam into a transitory coupling optic (55) linked respectively to the emitter (40) or to the receiver (30), these being fixed in relation to the ground (and therefore detached from the roll and not rotary) on one side, and to the roll shaft on the other. Protective means (310, 330) for this transitory aerial optical coupling may for example be provided using an isolating tube rigidly connected to the roll or the emitter or the receiver. This embodiment also makes it possible to avoid installing the emitter and the receiver in the cavity of the roll, and requires a simple electrically and optically "passive" adaptation in said cavity, which simplifies the design and maintenance of the roll.

Figure 6:
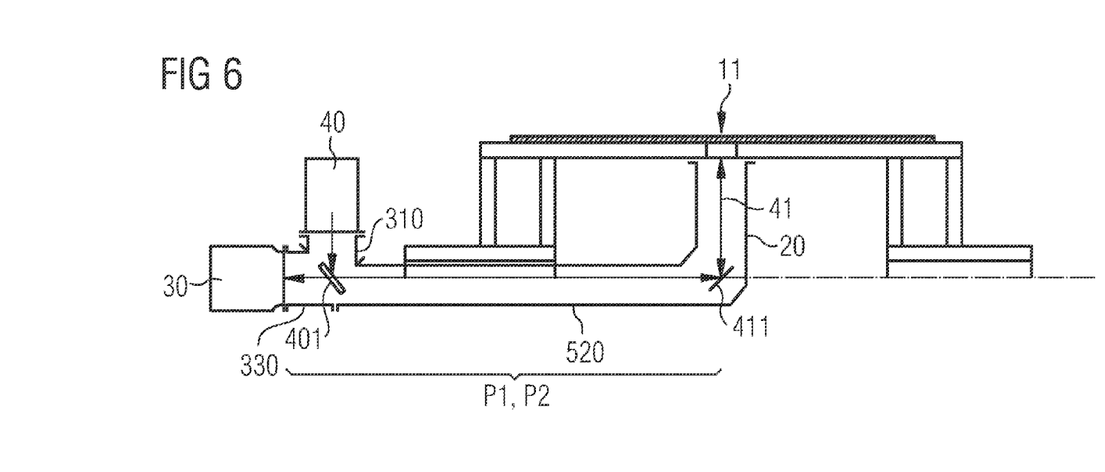

FIG. 6 shows a fifth embodiment according to FIG. 5, in that the emitter and the receiver are arranged outside the cavity of the roll, but in this case rigidly connected to the axis of rotation of the roll (by coupling means (310, 330) for a mechanical fixing to the axis of rotation of the roll, similarly to one of the roll extremities according to FIG. 6). This latter rigid connection is, however, not essential and may be precluded by the use of a coupling optic such as in FIG. 5 (where the elements 330, 55 would be detached). In this case, a decoupling rotary element is placed between the "coupling" elements (310, 330) and the air guide (520). It should be noted that the rigid connection of the emitter and the receiver to the roll or the shaft thereof provides the benefit of full offsetting of unwanted vibrations. Therefore, detachment of these elements from the roll would require coupling or uncoupling means that adequately offset vibrations. This is possible technically, but it complicates implementation.

In FIG. 6, the emitter and the receiver are also connected to a single optical route acting as the first and second optical routes (P1, P2), such as a simple aerial conduit (520) provided in the axis of rotation of the roll. A total reflection mirror (411) designed to cause optical incidence and feedback on/from the target point (11) is placed in the roll cavity, and intersects the aerial conduit at an angle of 45° from the principal direction of the aerial conduit (520) parallel (and identical) to the axis of rotation of the roll. A dichroic mirror (401) is arranged outside the cavity of the roll making it possible to channel the incoming and outgoing light beams between either the emitter or the receiver and the single aerial conduit (520). This arrangement enables the emitter, receiver and dichroic mirror (401) to be arranged as a single unit on the same side of the roll (rigidly connected thereto or otherwise), thereby facilitating implementation and maintenance of the roll and the measurement device itself. The junction between the single aerial conduit (520) and said single unit may be rotary to prevent the single unit from being driven in rotation with the roll.

Figure 7:
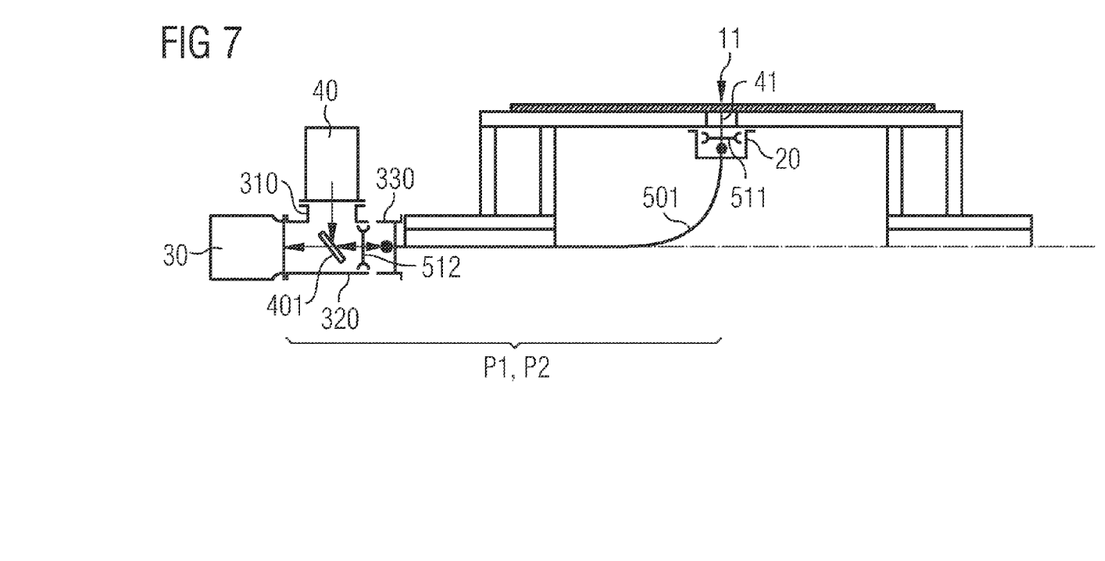

FIG. 7 shows a sixth embodiment according to FIG. 6, but in which the total reflection mirror (element 411 according to FIG. 6) is replaced by at least one optical fiber (501) (having a suitable bandwidth) or a bundle of optical fibers having an overall optical bandwidth that is able to send and receive the incident and feedback beams at the target point (11) using the ablation laser aimed by a single lens (511) at said point. A collimation optic (512) arranged between the dichroic mirror (401) outside the roll and the fiber or bundle of fibers (501) to couple it/them optically to the emitter and the receiver (40, 30). Identically to FIG. 6, an arrangement comprising the emitter, receiver and the dichroic mirror as a single unit is possible in order to enable a joint that can be uncoupled from a drive rotating by means of the roll.

The invention claimed is:

1. A device adapted for performing a spectral analysis of a metal coating layer deposited on a surface of a steel strip, the device comprising:
    a roller having a cylindrical wall with an outer-surface arc and surrounding a roller cavity, the steel strip being moved along said outer-surface arc and said cylindrical wall guiding the steel strip by contact;
    a laser ablation beam emitter having an output;
    a spectral plasma emission receiver having an input, said spectral plasma emission receiver is disposed inside said roller cavity of said roller;
    a first optical route disposed at said output of said laser ablation beam emitter and guiding a laser ablation beam through said roller cavity and having an optical guiding means to ensure an incidence of the laser ablation beam on a target contact point, said optical guiding means having a mirror or at least one optical fiber having a 90° elbow fully disposed within said roller cavity for guiding the laser ablation beam toward the target contact point;
    a second optical route disposed at said input of said spectral plasma emission receiver and collecting a spectral plasma emission distribution through said optical guiding means, said second optical route running at least partially through said roller cavity; and
    at least said optical guiding means being rotatable by a mechanical coupling synchronous to a rotation of said roller having said roller cavity.

2. The device according to claim 1, wherein said mirror is inclined at 45° from a normal axis and an axis of rotation of the roller.

3. The device according to claim 2, wherein said first optical route includes a light guide.

4. The device according to claim 2, wherein said second optical route includes a light guide.

5. The device according to claim 1, wherein said first and second optical routes have at least one optical fiber having a 90° elbow as said optical guiding means delimiting a fiber zone alongside an axis of rotation of the roller and a fiber zone alongside an axis normal to the target contact point.

6. The device according to claim 1, wherein at least one of said laser ablation beam emitter or said spectral plasma emission receiver is disposed outside of the roller cavity of the roller.

7. The device according to claim 1, wherein at least one of said laser ablation beam emitter or said spectral plasma emission receiver is coupled in synchronous rotation with said optical guiding means, in which case it is also coupled to an electrical link having a rotary joint for at least one of a power supply, a command signal or a control signal.

8. The device according to claim 1, wherein the roller has an opening formed therein formed as a porthole made of material that is optically transparent to the laser ablation beam and to spectral plasma emissions.

9. The device according to claim 2, wherein said mirror is dichroic.

10. The device according to claim 3, wherein said light guide is selected from the group consisting of an optical fiber and an air guide.

11. The device according to claim 4, wherein said light guide is selected from the group consisting of an optical fiber and an air guide.

* * * * *